US005360388A

United States Patent [19]

Spindel et al.

[11] Patent Number: 5,360,388

[45] Date of Patent: Nov. 1, 1994

[54] ROUND WINDOW ELECTROMAGNETIC IMPLANTABLE HEARING AID

[75] Inventors: Jonathan H. Spindel; Paul R. Lambert; Roger A. Ruth, all of Charlottesville, Va.

[73] Assignee: The University of Virginia Patents Foundation, Charlottesville, Va.

[21] Appl. No.: 958,737

[22] Filed: Oct. 9, 1992

[51] Int. Cl.[5] .......... A61N 1/00
[52] U.S. Cl. .......... 600/25; 607/55
[58] Field of Search .......... 128/420.6; 600/25

[56] References Cited

U.S. PATENT DOCUMENTS

| | | | |
|---|---|---|---|
| 3,594,514 | 7/1971 | Wingrove | 179/107 R |
| 3,764,748 | 10/1973 | Branch et al. | 179/107 E |
| 4,606,329 | 8/1986 | Hough | 128/421 |
| 4,612,915 | 9/1986 | Hough et al. | 128/421 |
| 4,817,607 | 4/1989 | Tatge | 128/419 R |
| 4,936,305 | 6/1990 | Ashtiani et al. | 128/420.6 |
| 4,957,478 | 9/1990 | Maniglia | 600/25 |

*Primary Examiner*—William E. Kamm
*Assistant Examiner*—Scott M. Getzow
*Attorney, Agent, or Firm*—Oblon, Spivak, McClelland, Maier & Neustadt

[57] ABSTRACT

An implantable hearing aid device including a vibrational element which is mounted to the round window of the cochlea and a transmitter which can be mounted externally of the ear or within the mastoid bone of the skull. The transmitter includes a microphone for picking up sound waves and converting the sound waves into electromagnetic signals which are imparted to the vibrational element fixed to the round window of the cochlea. The placement of the vibrational element on the round window provides significant advantages over conventional implantable hearing aids which transmit vibrational impulses to the oval window of the cochlea through a pathway which interferes with normal hearing. With the implantable hearing device of the present invention, the normal pathway used for receiving acoustically input sound waves is left unobstructed. With such an arrangement, two separate pathways are available for inputting vibrations to the cochlea, which allows constructive and destructive interference patterns to be set up between the acoustic wave vibrations and the magnetically induced vibrations. This allows the amplification of the signal components and canceling of the noise components.

9 Claims, 7 Drawing Sheets

RESPONSE AMPLITUDE (EM)

RESPONSE AMPLITUDE (ACOUSTIC)

ROUND WINDOW ELECTROMAGNETIC IMPLANTABLE HEARING AID

BACKGROUND OF THE INVENTION

1. Field of the Invention

The present invention relates to implantable prosthetic hearing enhancement devices which vibrate portions of the inner ear so as to stimulate the sensory apparatus which enables an individual to hear sound.

2. Discussion of Background

Over 22 million Americans, roughly one in every fifteen individuals, suffer from sensorineural hearing impairment or "nerve deafness." This condition affects approximately 80% of significantly hearing impaired patients, and unlike conductive hearing loss, cannot be surgically corrected. Current rehabilitation relies on conventional ear-canal hearing aids. Unfortunately, the use of those aids in nerve deafness involves frequent problems resulting from acoustic feedback or "squeal," poor sound quality, and inability to deal effectively with background noise. In normal auditory function, incoming sound causes vibration of the ear drumo. This vibration is carried by the chain of middle ear bones, or ossicles, to a spiral fluid filled structure known as the cochlea. Projecting into the cochlea are thousands of specialized cells, called hair cells, which connect to fibers of the auditory nerve. Vibration of the cochlear fluid results in deflection of microscopic fibers (stereocilia) on the surface of the hair cell. This stimulates the hair cells to initiate transmission of a neural signal via the auditory nerve to the brain. Damage to these hair cells can result from the aging process, noise exposure, head injury, infections, treatment with some medications, and hereditary factors, and is the most frequent cause of sensorineural hearing loss.

Currently, sensorineural hearing loss (SNHL) can be partially rehabilitated with "behind the ear" or "ear canal" type hearing aids. Conventional hearing aids amplify sound arriving at a microphone external to the ear and then send that high intensity sound from a small speaker in the car canal, through the air in the canal to the ear drum. Problems exist, however, in transmitting the amplified signal through the air in the canal and along the bones of the ear with the necessary intensity to overcome the sensorineural loss. Distortion of the sound and acoustic feedback to the microphone are the principal problems. Acoustic feedback at high hearing aid volumes requires that a tight fitting ear mold be used. This solution, however, often causes or aggravates infections in the ear canal and makes conventional aids for sensorineural hearing loss uncomfortable for long-term wear.

Research and development over the past two decades has identified implantable aids as a means for circumventing problems found in conventional (acoustic transmission) hearing aids. Implantable aids work on the basic principle that vibrational energy can be directly imparted to the middle or inner ear through non-acoustic transmission. These methods require the use of an implanted vibrator connected to some structure of the middle ear or inner car which when displaced can produce vibrations that reproduce those generated in normal hearing. Implantable vibrators in use today utilize either a piezoelectric ceramic bimorph or an electromagnetic-permanent magnet couple.

Piezoelectric bimorphs consist of a bonded pair of piezoelectric materials. Piezoelectric materials lengthen or shorten with axially applied current. In the bimorph, two bonded pieces of piezoelectric material are oppositely aligned, so that when current is applied, they will deflect maximally in one direction or the other dependent on the polarity of the current. As an implant, the bimorph can have one end anchored to the skull with the other attached by some means to the ossicular chain in the middle ear. In this way electrical energy from an amplified signal can be transduced into vibrational energy in the middle ear system by non-acoustic transmission. To a large extent, research utilizing this approach has been conducted, see, for example, Gyo, K., Goode, R. L., Miller, C.: "Stapes Vibration Produced by the Output Transducer of an Implantable Hearing Aid", *Arch. Otolaryngol. Head and Neck Surgery,* Vol. 113, pp. 1078–1081 (1987), and Yanagihara et al, "Implantable Hearing Aid Using an Ossicular Vibrator Composed of a Piezoelectric Ceramic Bimorph: Application to Four Patients" *American Journal of Otolaryngol.,* Vol 8, pp. 213–219 (1987). These groups have produced good results, but there are inherent problems with this approach. The piezoelectric implant totally disrupts the normal middle ear mechanism due to its attachment to the ossicular chain. These bones are no longer free to vibrate in response to incoming acoustic energy. Additionally, a means is required to transport the electric signal from the hearing aid's external pickup microphone and amplifier to the implanted device. Yanagihara et al. (1987) have attempted to solve this problem by using electromagnetic induction across the skin. This method, while somewhat effective also introduces additional transduction and amplification steps, with degradation of performance.

Hough et al., in "A Middle Ear Implantable Hearing Device for Controlled Amplification of Sound in the Human: A Preliminary Report" *Laryngoscope,* Vol 97, pp. 141–151 (1987), describe results obtained using magnet placements on the ossicles of the middle ear of animals and five implantation patients. The results reported in that study clearly indicate the potential benefits of this type of aid, but the degree of hearing enhancement achieved was less than that required for the rehabilitation of severe sensorineural hearing loss. Their approach relied on a magnet attached to an ossicle of the middle ear. That approach is restricted in its ability to deliver high amplitude vibrational energy to the inner car. Our pilot studies show that direct stimulation of the inner ear is achievable using a round window magnet. A device to significantly aid in the rehabilitation of moderate to severe sensorineural hearing loss must provide extremely high gain. Signal gain must also be accompanied by proper signal processing to achieve the flexibility and signal characteristics necessary for maximized sensorineural hearing loss rehabilitation.

In U.S. Pat. No. 3,764,748 there is disclosed an implantable hearing aid device which vibrates the cochlea using a bimorph crystal which imparts vibrations corresponding to sound waves entering the ear canal and vibrating the eardrum and/or ossicular bones. However, this technique has the disadvantage that artificial devices must be connected to the delicate structures of the normal acoustic input pathway. The device of the present invention avoids this drawback using an implementation which leaves the normal acoustic pathway and delicate structures associates therewith unobstructed by artificial devices, e.g., coils, microphones, etc.

SUMMARY OF THE INVENTION

Accordingly, the present invention has as its objective to provide an implantable hearing device that overcomes the problems of conventional hearing aids in the treatment of nerve deafness. The approach employs electromagnetic force transmission in place of the acoustic transmission of the conventional hearing aid. A tiny magnet is surgically placed on the round window of the inner ear and its motion is driven by a small electromagnetic coil transmitter. This technique of signal transduction appears to have five key advantages over conventional aids and other implant approaches. First, the problem of acoustic feedback is completely eliminated, because the amplified transmission is magnetic and not acoustic energy. In the prior art, conventional aids have generated acoustic feedback when used at the high amplification levels needed for nerve deaf listeners. The configuration of the conventional aid places a sensitive microphone (the input transducer) just outside the ear canal. This received sound is amplified and applied to the eardrum through an acoustic output transducer in the canal. This method of amplified energy delivery to the ear frequently creates a condition of acoustic squeal, where the amplified sound "feeds back" to the microphone.

A second advantage of the inventive hearing aid is that the direct transmission to the inner ear provided by the implantable magnetic device eliminates the serial stages of signal degradation that occur at the output transducer and in the middle ear system when operating at the levels of acoustic transmission used in high-gain conventional aids.

Third, the implantable aid by-passes the ear canal, leaving the canal in its normal, open condition. This eliminates the propensity for infection, the discomfort, and the difficulty of maintaining stable performance when the performance depends on a tight seal that blocks the ear canal. By leaving the ear canal open the implantable device also eliminates the cosmetic problems that limit use of aids in the general population. Also, by leaving the normal acoustic input pathway unobstructed by any artificial electromagnetic devices, the individual's natural hearing mechanism can continue to function, while the inventive implantable aid functions in conjunction with the natural hearing process in order to supplement natural hearing, instead of completely substituting for it as in conventional devices.

Fourth, the round window placement of the magnet leaves the ossicular chain in the middle ear undisturbed, so that after implantation two paths of signal transmission to the cochlea will exist. This provides freedom from erosion to the delicate ossicles, the persistence of a functional ossicular chain, so that hearing is not totally dependent on the implant, and the potential to use the implant as a modulator that assists detection of signals transmitted through the normal outer and middle ear ossicular apparatus.

Fifth, the implantable device has the potential to use digital signal processing applied to the incoming signal to provide precise and flexible means for eliminating frequency specific and broad spectrum background noise.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
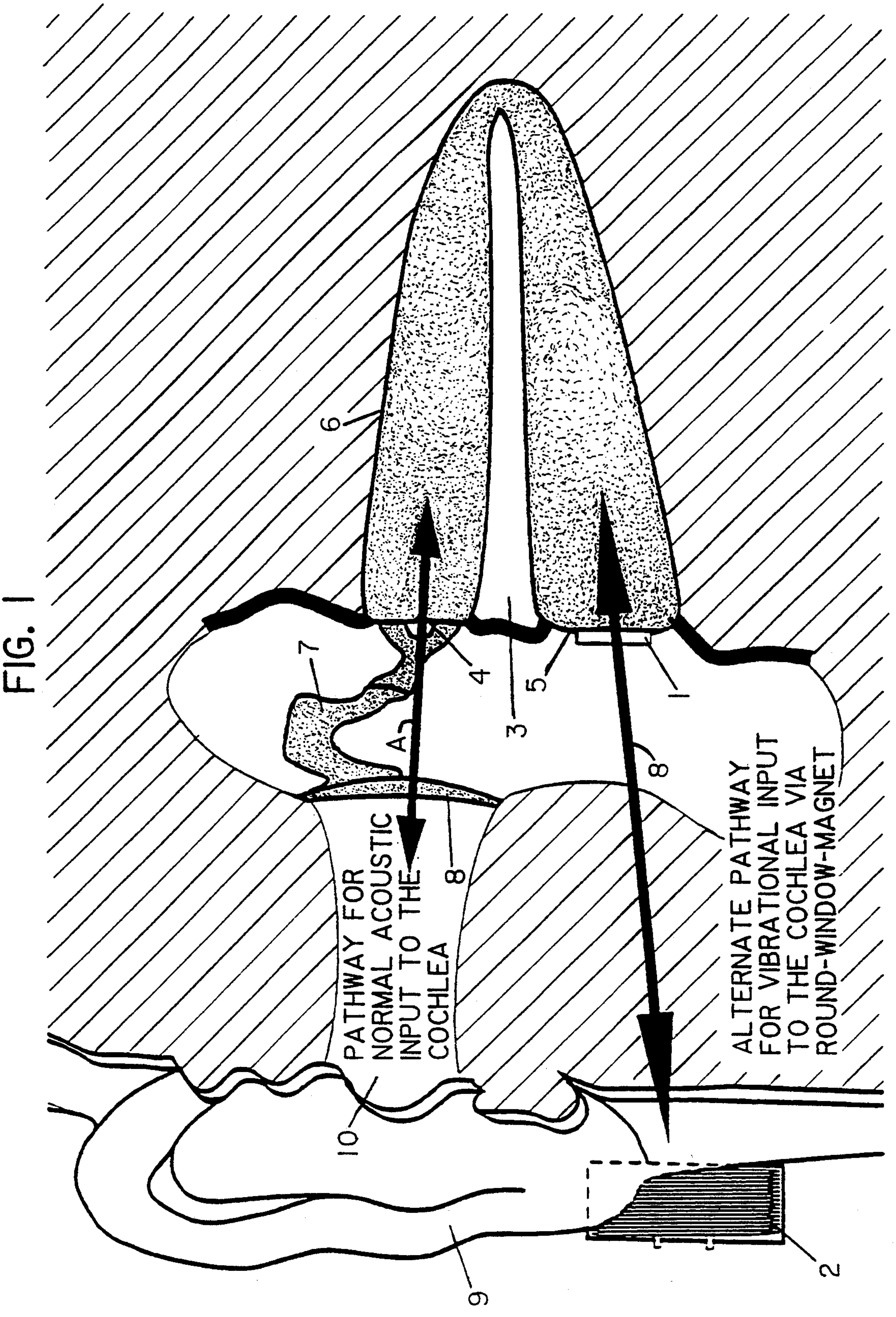
FIG. 1 shows a preferred embodiment of the Round Window Electromagnetic (RWEM) hearing aid device according to the present invention.

Referring now to the drawings, wherein like numerals designate identical or corresponding parts throughout the several figures, and more particularly to FIG. 1 thereof, there is shown in FIG. 1 the general arrangement of the inventive hearing aid device. The vibrational element is represented by numeral 1 which is shown securely fixed to the external surface of the round window 5 of cochlea 6. A basilar membrane 3 is shown between the two longitudinal leg portions of the cochlea 6. Also seen is oval window 4 where normal acoustically input sound wave vibrations enter the cochlea in order to stimulate the sensory nerves for producing the sensation of sound, as will be described in more detail below. Normal acoustic sound waves enter the ear 9 and pass through the ear canal 10, striking against eardrum 8. The eardrum vibrates, and these vibrations are imparted to ossicular bones 7 which in turn vibrate the oval window 4 of the cochlea 6. Vibrational element 1 can be any type of electric or electromagnetically sensitive material, such as a permanent magnet, piezoelectric element, etc. The inventive hearing aid device has a transmitter 2 which can be mounted externally of the ear 9, or in an alternative embodiment, the transmitter 2 can be mounted internally within the mastoid bone of the skull, as long as the pathway from the transmitting device to the vibrational element does not overlap with the pathway used for normal acoustic hearing processes.

There are thus two separate pathways for the acoustic and electromagnetic waves to travel on in order to reach the cochlea 6 along path A. The electromagnetic waves are transmitted to the vibrational element 1 along path B, while the acoustic waves enter ear canal 10 and are imparted to the eardrum 8, ossicular bones 7 and oval window 4 of the cochlea 6. In this manner, two distinct sources of vibration are imparted to the cochlea 6, one being the individual's normal hearing input, and the other being the artificially induced vibrations caused by the transmitter 2 picking up sound waves using any type of conventional pickup microphone, and outputting electromagnetic signals to the vibrational element attached to the round window 5 of the cochlea 6. Therefore, by varying the phase and/or frequency of the electromagnetic waves imparted to vibrational element 1, constructive or destructive interference patterns between the natural vibrations imparted to the oval window 4 and the artificially induced vibrations imparted to round window 5 can be controlled in order to obtain optimum gain characteristics of the hearing aid and/or to filter out background noise components.

Figure 2:
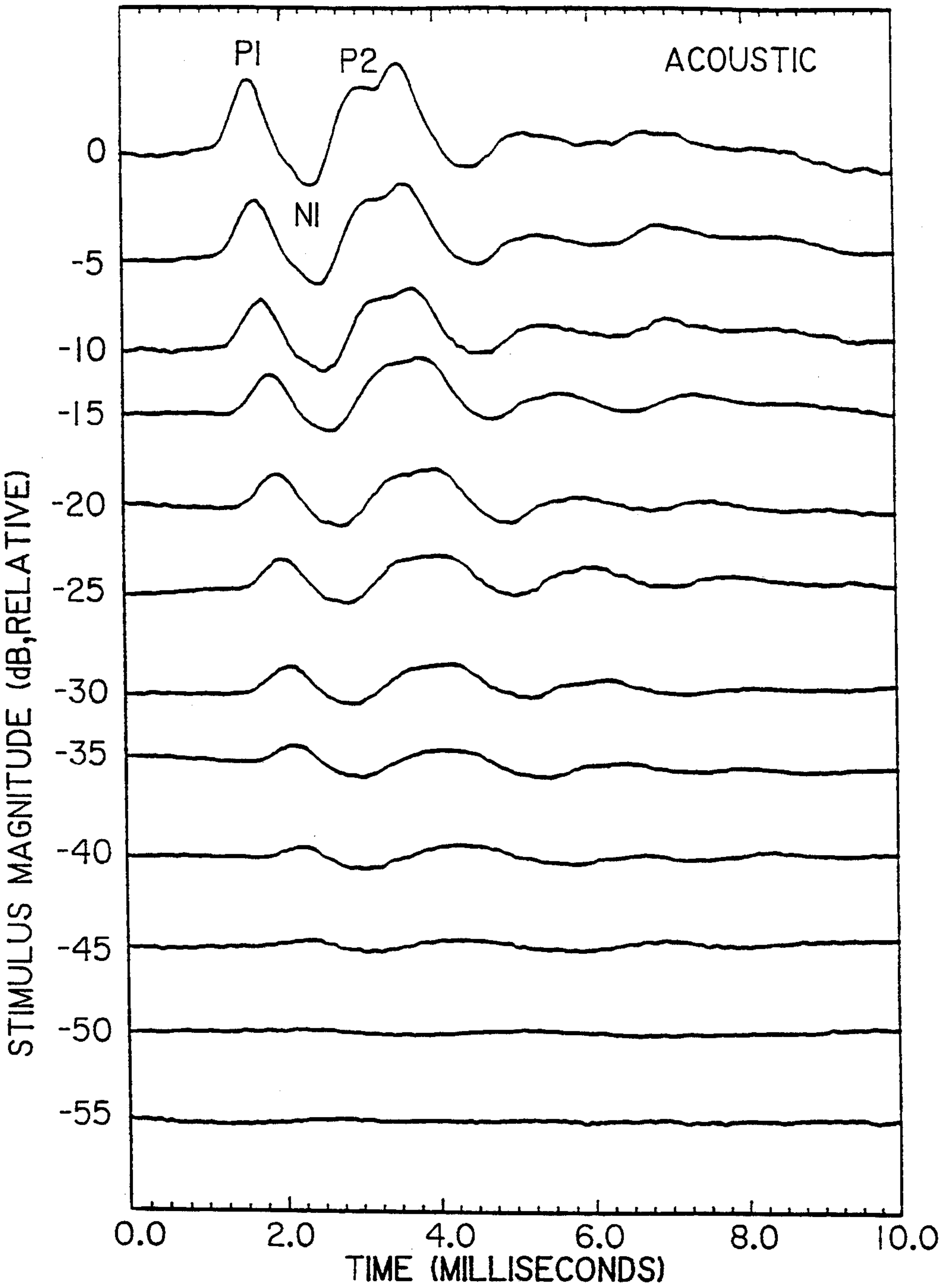
FIG. 2 illustrates acoustically evoked auditory brainstem responses obtained from a guinea pig having a round window magnet in place. Acoustic clicks of 50 microseconds duration and various intensities were applied.

FIG. 2 illustrates acoustically evoked auditory brainstem responses (ABRs) obtained during experiments using a permanent magnet as the vibrational element mounted on the oval window of a guinea pig. Acoustic clicks were transmitted for 50 microseconds durations at several decibel levels ranging from −55 dB to 0 dB. The graph shows very slight response beginning at −45 dB and progressively increasing with increased intensity level of the clicks, as expected.

Figure 3:
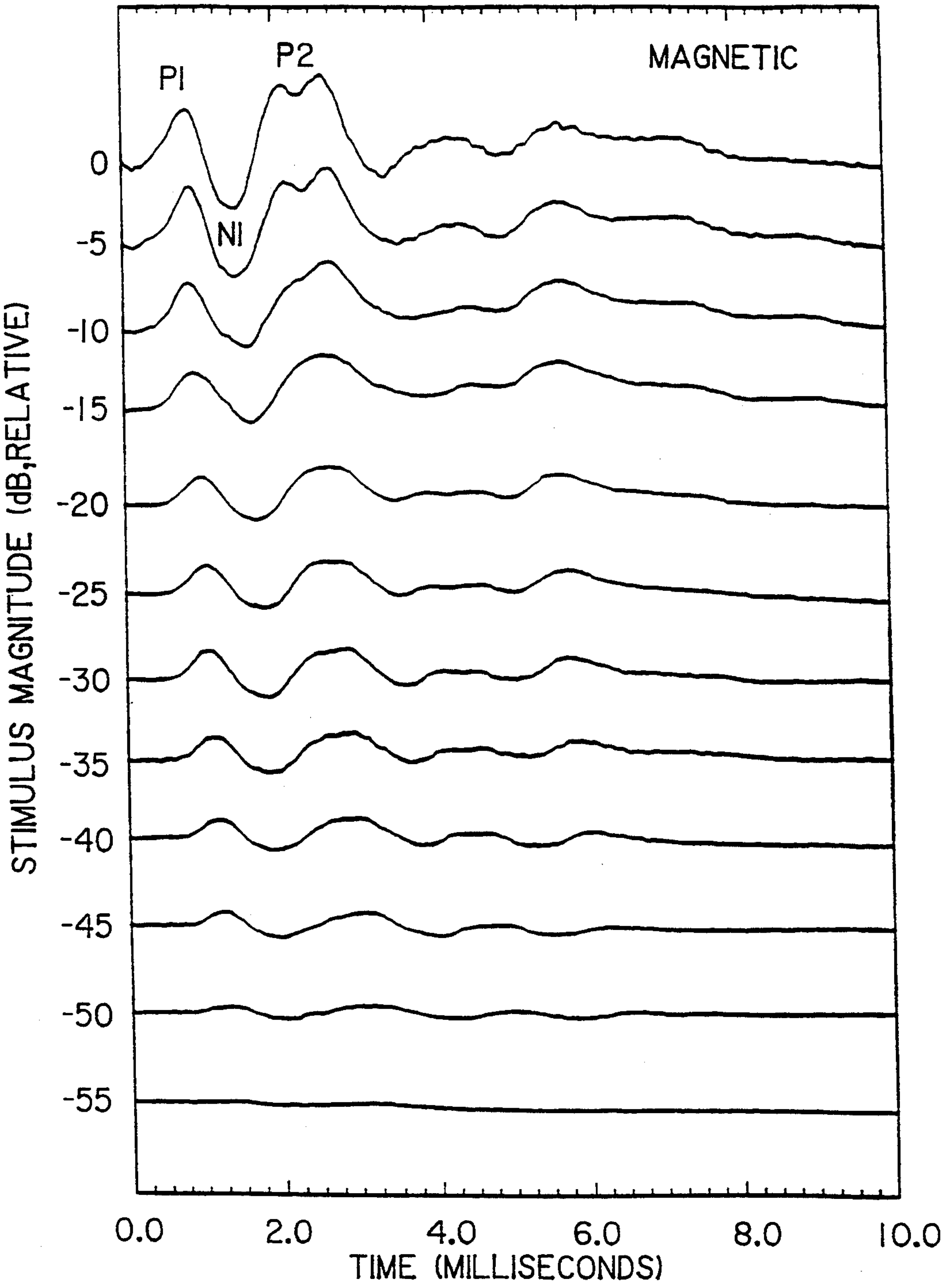
FIG. 3 illustrates magnetically evoked auditory brainstem responses from the same implanted guinea pig referred to in FIG. 2.

FIG. 3 illustrates the magnetically evoked ABRs using the same implanted permanent magnet placed on the round window of the guinea pig corresponding to the acoustically evoked ABRs of FIG. 2. The observed time shift of the magnetic ABRs with respect to the acoustic ABRs corresponds to the travel time of sound during acoustic stimulation that is not present during magnetic stimulation.

In order to measure the increase in efficiency of transmission of energy to the inner ear by the use of electromagnetic induction as compared to acoustic transmission, a small magnet was placed on the ear drum of a guinea pig. An electromagnetic induction coil was placed in the ear canal about 4 millimeters from the ear drum. With this arrangement, the experiments were able to preserve fidelity and eliminate the problem of acoustic feedback and squealing at high volumes. It is not possible, however, to maintain a magnet on the ear drum long-term due to the continual loss of surface epithelium and environmental exposure. Various placements of magnets within the middle ear were tested and a base of preliminary data was established. This analysis of the problem led to the unique approach to the issue of magnet placement.

Placement of the magnet on the round window of the cochlea allows the enhancement of desired auditory signals, such as speech, as well as the cancellation of undesired acoustic noise. The frequency of vibration of the vibrational element can be adjusted so that the signal components of sound waves entering the cochlea can be amplified, whereas noise components are filtered out. Long-term bone erosion resulting from placing a magnet on an ossicle is also eliminated and full preservation of the existing functional middle ear system is permitted. A much larger area for placement of the electromagnetic device, in the bony area behind the ear, leaves the possibility open for total implantable hearing aid development. This approach differs significantly from those currently investigated by others, promising more comprehensive management of signal enhancement, noise cancellation, and the eventual development of a totally implantable digital hearing aid.

As a means to initially evaluate this approach, a number of guinea pigs were implanted with "round window magnets." Auditory brainstem responses (ABR) were recorded from these animals before and after implantation. As seen from FIG. 3, the ABRs obtained via electromagnetic induction are similar in form to acoustically evoked ABRs. These data confirm the feasibility of our approach. Additionally, we explored the ability of the vibrations of a round window magnet (RWM) to interfere with a normal acoustic input through the middle ear. Both input pathways were operated simultaneously with signals slightly out of phase.

Figure 4:
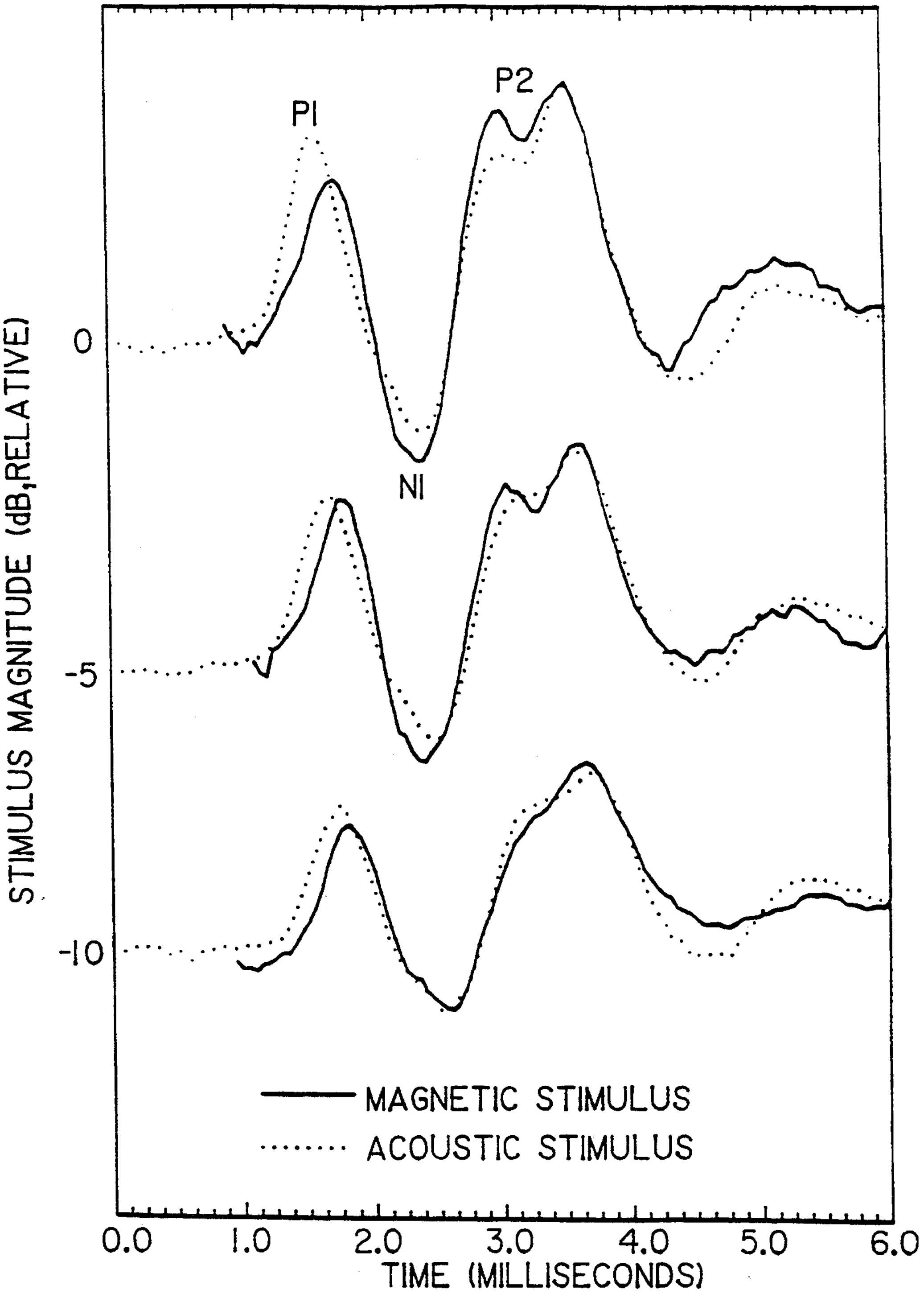
FIG. 4 shows that the magnetic ABRs were obtained by adjusting the electrical signal until equivalent peak-to-peak amplitudes were observed with respect to the acoustic responses. Overlaying equivalent waveforms from the acoustic and magnetic responses allows for direct comparison of the responses.
Figure 5A:
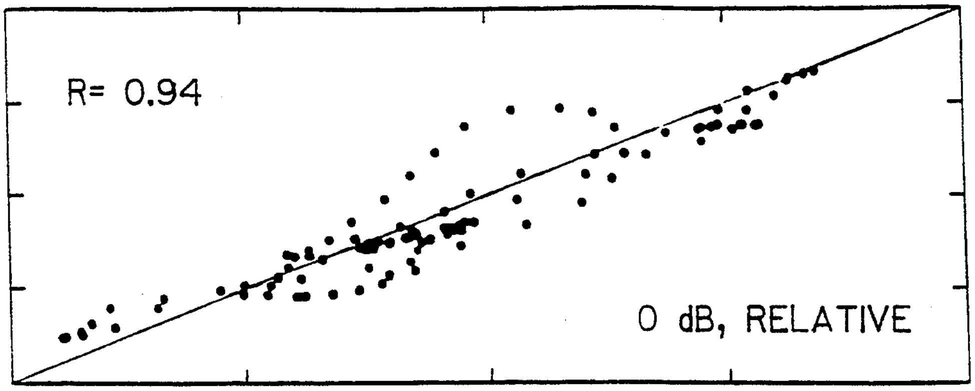
FIG. 5 illustrates scatter plots and correlation calculations (r) of the waveform sets shown in FIG. 4, depicting a high degree of correlation for all three data sets.
Figure 5B:
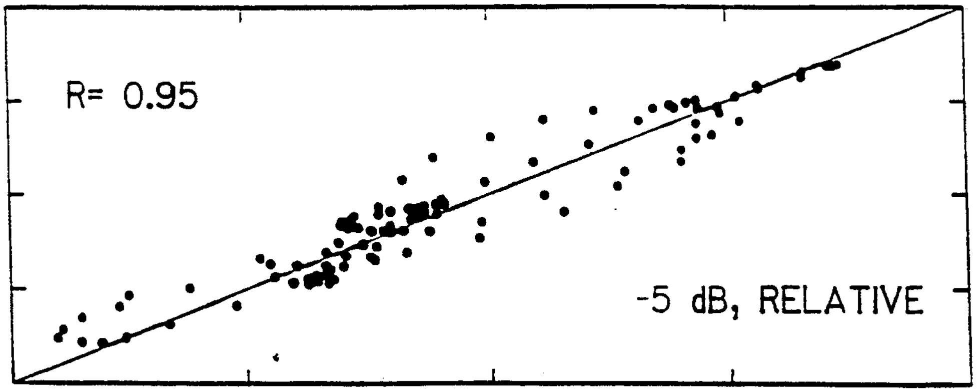
Figure 5C:
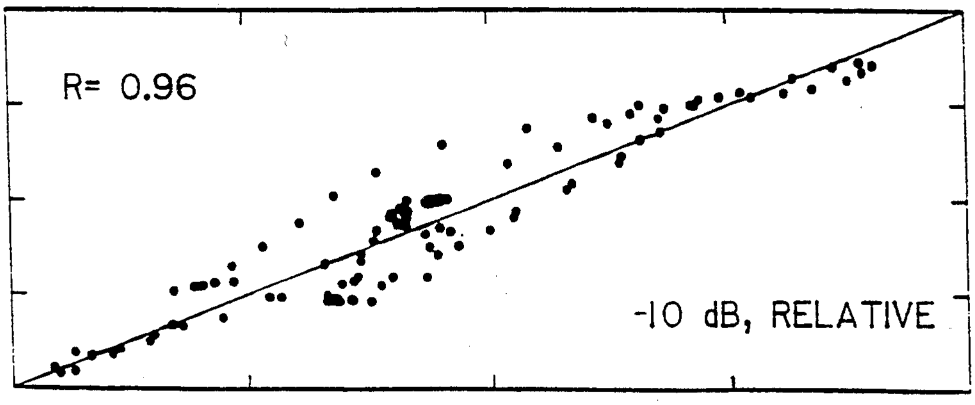

The top three traces of the acoustic and magnetic responses from FIGS. 2 and 3 are shown in FIG. 4 with the magnetic response shifted so as to compensate for added travel time of the acoustic signal. A high degree of correspondence is evident. Correlation coefficients and scatter plots of response amplitudes are shown in FIG. 5.

Figure 6:
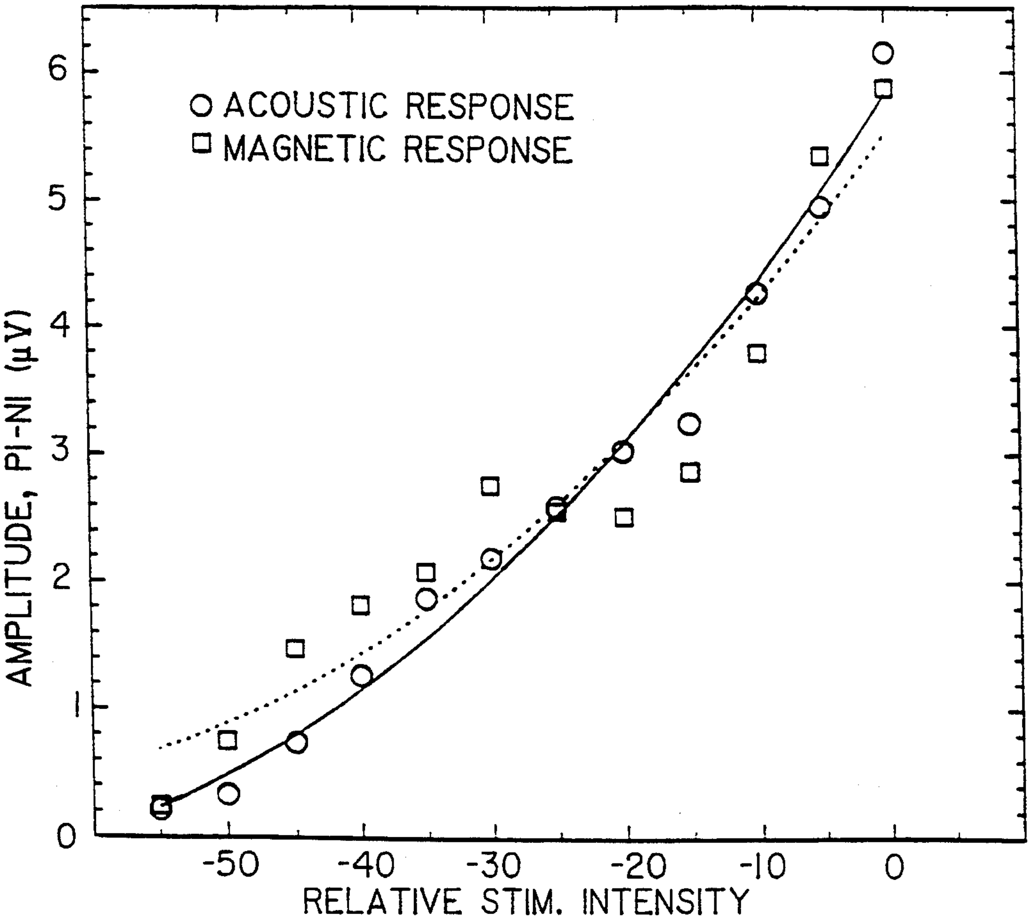
FIG. 6 shows peak-to-trough (P1-N1) amplitude as a function of stimulus intensity for the acoustic and magnetic responses of FIGS. 2 and 3.
Figure 7:
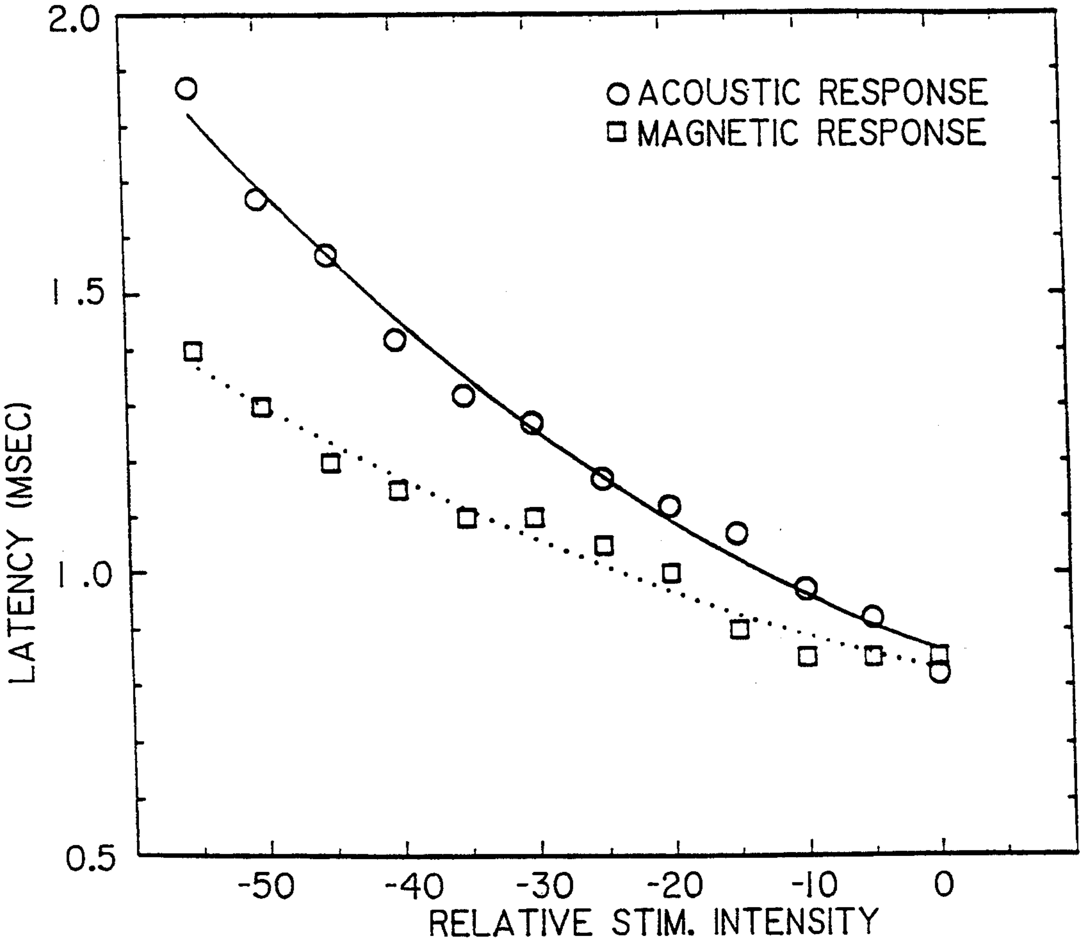
FIG. 7 shows the latency of the P1 peak potential as a function of stimulus intensity for the acoustic and magnetic responses of FIGS. 2 and 3.

Peak ABR amplitudes versus intensity for the magnetic and acoustic stimuli are graphed in FIG. 6. The amplitudes are derived from the peak to trough (P1-N1) amplitude measured at each stimulus intensity level. As expected, the amplitudes of the responses increased with increasing stimulus intensity and the rate of increase is comparable for the two modes of stimulation. The latencies of P1 versus the intensities for the stimuli are graphed in FIG. 7. The latencies of these responses decrease with increasing stimulus intensity, as expected. The Round Window Electromagnetic (RWEM) latency, however, decreases more slowly as a function of increased magnetic intensity as compared to that of the acoustic response data.

The validity of the RWEM approach was supported by the measurements of ABRs evoked by acoustic and magnetic stimuli. Correlation coefficients and the correspondence between the peak P1 amplitudes measured as functions of stimulus levels provided quantitative support for the proposal that RWEM stimulation could mimic acoustic stimulation. It is important to note, however, that while click-evoked responses can provide valuable information pertaining to the broadband frequency response of the auditory system, those stimuli result in measures that provide little frequency-specific information. Limited frequency-specific information, however, can be obtained from the latency versus intensity curves illustrated in FIG. 7.

The lower rate of latency change with increasing stimulus intensity for the RWEM responses (smaller slope) suggests that the RWEM stimulus may have a flatter frequency response than the acoustically delivered stimulus. At higher stimulus intensities, the short latency ABR arises from synchronous activity in the more basal (higher frequency) regions of the cochlea. As stimulus intensity is decreased, the activity arises from the more sensitive, mid-regions of the cochlea, and the latency increases. The shorter latency of the RWEM response, at low intensities, as compared to the acoustic response, indicates that at those low stimulus intensities, higher frequency regions of the cochlea are still driven. A possible explanation for this observation is that the broadband acoustic click is low-pass filtered by the free-field acoustics of the sound delivery system and the band-pass nature of the outer and middle ear. The EM input by contrast, directly drives the round window magnet. The frequency response of this "vibration" delivery system is limited only by the high-pass characteristics of the coil (15 kHz) and some mechanical interface properties at the round window. It is believed that the input to the cochlea from the RWEM minimizes interface effects on the delivered signal and therefore can provide greater bandwidth and flatter response than acoustic inputs.

The inventive device provides a means of creating a middle ear implant that requires no electronically active implanted components. The use of electromagnetic induction for the direct transduction of the electrical signal into vibrational energy eliminates the problem of signal delivery from the external pickup across the skin. Additionally, since the implanted permanent magnet does not require a fixed base, normal middle ear function will not be disturbed at all using a round window magnet.

A major concern of the present invention was establishing an optimal electromagnetic coil design to be coupled to the implanted permanent magnet. The system was designed under the assumption that to minimize the effect of the magnet weight on the resonating cochlear fluid system, the permanent magnet should be designed to be minimally massive. This concern also applies indirectly in the realization that the guinea pig round window is on the order of 1 millimeter in diameter. For the round window application, the magnet should be minimized with respect to size in order to minimize its effect on the window compliance when attached. With these two considerations in mind, an early prototype transduction system was designed so as to provide maximal electromagnet energy delivery, and a maximal permanent magnet magnetism-to-mass ratio. The latter criterion was satisfied by utilizing a neodymium-iron-boron magnet. This material, while somewhat difficult to work with due to its brittle nature, maintains an ultra-high permanent magnetic field energy on the order of 40 million Gauss-oersteds. With this material at our disposal, 0.05 millimeter slices were made on a diamond saw, and chips of approximately 0.5 millimeter square were shaped under a microscope.

The electromagnetic coil design required that attention be given to the high-frequency attenuation characteristics of the coil acting as an inductor. Since the transmitted magnetic field to the implanted magnet is dependent on current, the transfer function is derived from the input voltage to the coil as compared to the output coil current. The resulting transfer function thus yields a linear system of low-pass response. The coil design must be such as to provide maximal magnetic field strength while maintaining the required bandwidth. our design calls for a bandwidth of approximately 15 kHz. Other factors defining the magnet field strength of the coil include the coil radius, r, the number of turns, N, and the axial distance from the coil. The formula for the far-field magnetic field strength along the axis of an electromagnetic coil is given by:

$$B = \frac{\mu o}{2 \cdot \pi} \cdot \frac{N \cdot i \cdot A}{x^3} = \frac{\mu o}{2} \cdot \frac{N \cdot i \cdot r^2}{x^3}$$

This indicates that while the number of turns, the coil current and the radius define increasing magnetic field, an overriding factor is the axial distance. The magnetic field will decrease with the cube of this distance. The coil must, therefore, be designed for maximal magnet field strength by controlling r and N, while still maintaining a reasonable size. The inductance of the coil, and thus its low-pass effect, is defined primarily by N.

Various approaches have been studied concerning the establishment of a biocompatible long-term means of attaching the implanted magnet to the round window, including culturing a biological membrane around the magnet and grafting the grown tissue culture onto the round window of the cochlea, so that a biomechanical interface exists between the moving magnet and the cochlear fluid. It is in the cochlea that mechanical vibrations passed via the tympanic membrane, ossicular chain, and oval window are transduced to neural input. Frequency resolution in the cochlea is due to a travelling wave which arises in the basilar membrane of the cochlea due to vibrations of the cochlear fluid. This wave reaches a maximum displacement at a characteristic length along the basilar membrane dependent upon the frequency of the input signal to the system.

By selectively enhancing or degrading portions of the captured acoustic signal a vibrational input to the round window can be developed. This input can be tuned to compensate for cochlear spectral deficiencies present in sensorineural hearing loss. Digital signal processing techniques allow the greatest flexibility and precision for such fine manipulations of frequency spectra and, therefore, would be the method of choice for this development. Initially the development will be performed totally in software, however due to the real-time processing nature of this operation, the eventual shift to a digital hardware environment will be required. Further investigation will proceed to define the transfer function of the inner ear system as completely as possible. This will be used to analyze the precise effects of round window compliance as altered by the placement of the implant and its accompanying mass. This knowledge will also allow for the development of a more precise end-to-end model for the entire prosthetic system.

The inventive hearing aid device described above relies on the use of electromagnetic induction to remotely transmit vibrational energy to a magnetic implant in the ear, by using a transmission pathway separate from the normal acoustic pathway. This approach has been shown to have the following solutions to problems associated with conventional hearing aids:

(1) Acoustic feedback is eliminated since the form of the amplified transmission is magnetic and not acoustic energy. Conventional hearing aids generate this "squeal" due to amplified acoustic energy "feeding back" to the microphone.

(2) Direct transmission to the inner ear maintains sound quality by eliminating signal degradation in the output and the middle ear system at the overdriven levels of acoustic transmission used in high gain conventional hearing aid devices.

(3) Digital signal processing techniques applied to the incoming signals have the potential to provide a precise and flexible way to eliminate both specific frequency and broad spectrum background noise.

(4) The implantable aid by-passes the ear canal, leaving the canal in its normal, open condition thereby eliminating the propensity for infection, discomfort, and other problems associated with ear canal blockage which exist in the prior art hearing aid devices.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for enhancing hearing by artificially vibrating inner portions of the ear in order to stimulate the sensory nerves which enable an individual to hear sound, comprising the steps of:

placing a fixed transmitting means at a location remote from a first pathway used for normal acoustic hearing, said first pathway including the individual's ear canal, eardrum, ossicular chain and oval window of the cochlea;

attaching a vibrational means to the round window of the cochlea in the inner ear of the individual; and vibrating the cochlea through the round window using a second alternate pathway such that the first pathway for normal acoustic hearing is free of any artificial devices and electromagnetic waves are output by said fixed transmitting means and reach said vibrational means via a second alternate pathway to the cochlea located at a location remote from said first pathway, thereby providing two separate pathways for vibrations to be transmitted to the cochlea.

2. The method according to claim 1, further comprising the step of creating constructive or destructive interference patterns in order to enhance the volume of sound perceived by the individual.

3. The method according to claim 1, further comprising the step of picking up sound waves using a microphone in order to generate said electromagnetic waves which are to be received by said vibrational means.

4. The method according to claim 1, further comprising the step of attaching a permanent magnet to the round window of the cochlea by means of a tissue graft.

5. The method according to claim 4, wherein said step of attaching the permanent magnet to the round window of the cochlea includes the step of culturing a biological membrane around the permanent magnet.

6. The method according to claim 1, further comprising the step of attaching a piezoelectric element to the round window of the cochlea by means of a tissue graft.

7. The method according to claim 6, wherein the step of attaching the piezoelectric element to the round window of the cochlea includes the step of culturing a biological membrane around the piezoelectric element.

8. The method according to claim 1, further comprising the step of mounting said transmitting means behind the ear of the individual.

9. The method according to claim 1, further comprising the step of mounting said transmitting means within the mastoid bone of the skull.

* * * * *